United States Patent [19]
Simon

[11] Patent Number: 5,635,623
[45] Date of Patent: Jun. 3, 1997

[54] DEVICE AND METHOD FOR MEASURING RESISTANCE TO ROLLING AND ADHERENCE LIMITS

[75] Inventor: Jean-René Simon, Clermont-Ferrand, France

[73] Assignee: Compagnie Générale des Etablissements Michelin-Michelin & Cie, Clermont-Ferrand Cedex, France

[21] Appl. No.: 446,634

[22] PCT Filed: Aug. 16, 1994

[86] PCT No.: PCT/EP94/02718

§ 371 Date: May 8, 1995

§ 102(e) Date: May 8, 1995

[87] PCT Pub. No.: WO95/07456

PCT Pub. Date: Mar. 16, 1995

[30] Foreign Application Priority Data

Sep. 10, 1993 [FR] France .................................. 93 10953

[51] Int. Cl.⁶ .......................... G01N 19/02; G01M 17/06
[52] U.S. Cl. ............................................. 73/9; 73/146
[58] Field of Search ................................. 73/9, 146

[56] References Cited

U.S. PATENT DOCUMENTS

| | | | |
|---|---|---|---|
| 3,367,170 | 2/1968 | Lynch et al. | 73/9 |
| 4,144,748 | 3/1979 | Vinogradov et al. | 73/9 X |
| 4,173,885 | 11/1979 | Matlock | 73/9 X |
| 4,909,073 | 3/1990 | Takahashi et al. | 73/9 X |
| 4,955,933 | 9/1990 | Sistonen | 73/9 |

FOREIGN PATENT DOCUMENTS 1227807  8/1960  France .

OTHER PUBLICATIONS

Journal of Testing and Evaluation, vol. 20, No. 6, Nov. 1992, Philadelphia, PA, US, pp. 470–474, Siew–Ann Tan et al. "Laboratory Wheel Tracking Apparatus for Bituminous Pavement Studies".

Soviet Inventions Illustrated Week 8938, 6 Sep. 89 Derwent Publications Ltd., London, GB; AN 89–218769/30 & SU 1434–334–A (Sarat Poly) 30 Oct. 1988.

*Primary Examiner*—Thomas P. Noland
*Attorney, Agent, or Firm*—Brumbaugh, Graves, Donohue & Raymond

[57] ABSTRACT

A device in which two identical mounted assemblies E are assembled by a connecting arm which is provided with ballasting means (7) such that the center of gravity G of the loaded device is located below a straight line ZZ' connecting the centers of rotation of the two assemblies E. The device is rotated to impart a cycloidal movement to the center of gravity G to a given angular position. A method of using such devices for carrying out methods of comparative measurements of resistances to rolling and adherence properties of at least two sets of tires or the same properties on at least two types of travel surfaces.

13 Claims, 6 Drawing Sheets

FIG 6

DEVICE AND METHOD FOR MEASURING RESISTANCE TO ROLLING AND ADHERENCE LIMITS

BACKGROUND OF THE INVENTION

The present invention relates to a device which makes it possible to determine the forces present between the tire and the travel surface on which it is rolling and furthermore, in particular, permits measurement of the properties of the tire, utilizing the longitudinal forces. Such properties are, for instance, the rolling resistance and the coefficient of longitudinal adherence. The invention also concerns the methods carried out by means of such a device and, more particularly, the methods for the comparative measurement of the properties of rolling resistance and adherence limits of different tires, or the same properties due to different travel surfaces.

Taking into account all the factors which can play a part during the measurement of rolling resistance, this measurement is very difficult and, as known, there are two major kinds of methods: The first kind concerns measurements on machines, and mention may be made of measurements on a flywheel, the tire to be tested traveling on a flywheel of larger or smaller diameter, and measurements on roller test benches, said rollers having small diameters and producing stresses in the tire far different from those encountered on a flat travel surface, hence the appearance of the machine on a flat travel surface in the form of a belt on which the tire rolls; the second type concerns measurements on actual runways and travel surfaces which are generally carried out with a vehicle, whether an analytical vehicle or a conventional vehicle. With this last type of vehicle, the so-called travel-surface-deceleration method is frequently used, which method is undoubtedly less precise than the others, but gives interesting results, since it includes the environmental factors to the maximum extent.

As to the adherence limit measurements, they are also generally carried out with the use of flywheels in the case of measurements on machines, but they are more frequently performed with the use of vehicles traveling on runways with different variable, travel surfaces. It is obvious that the methods with vehicles and runways require considerable space, in the same way as the methods with flywheels, since the flywheels must be of large diameter.

SUMMARY OF THE INVENTION

The object of the invention is to provide a device which, while simple, permits at least a comparative measurements of rolling resistances and/or of adherence limits within a limited space, or at least a space which is very small as compared with runways or workshops, while permitting rolling on a flat travel surface or one of very little curvature.

The device in accordance with the invention is characterized by the fact that it comprises two dimensionally identical mounted assemblies, assembled by a connecting arm the center axis of which is parallel to the straight line connecting the centers of rotation of the unloaded mounted assemblies, said connecting arm being provided with ballasting means necessary for obtaining the load imposed on each of the assemblies and such that the center of gravity of the device at rest is located between said straight line and the travel surface on which the device will roll, the device furthermore comprising means capable, by rotation of the mounted assemblies, of imparting to its center of gravity a cycloidal movement giving it a given angular position with respect to the plane containing the straight line connecting the centers of rotation of the mounted assemblies which is perpendicular to the travel surface.

By mounted assembly there is to be understood the assembly formed by at least one tire inflated to a given pressure and its mounting rim, said rim being provided with a wheel disk which can be fastened on a hub. The connecting arm which connects the two mounted assemblies can be a rigid connecting bar of any cross section, for instance circular or square, fastened firmly on the two hubs on which the disks themselves are fastened. This arm will advantageously be an arm which can turn freely in the housings provided for this purpose in the hubs and disks of the mounted assemblies. It being pointed that the expression "parallel to" is intended to include "merged with," the connecting arm will preferably be the axle of rotation the center line of which, which is the axis of symmetry, is the straight line joining the centers of rotation of the mounted assemblies.

As to the means capable of conferring a cycloidal movement on the center of gravity of the device, radially below the straight line connecting the centers of rotation of the mounted assemblies, they may be of different types. The movement of rotation of the mounted assemblies may be the result of the application of a tractive force on the axle connecting the centers of rotation of the mounted assemblies and freely turning in the hubs. This movement may also be the result of the application to the two assemblies of a moment of rotation which is imposed manually of mechanically. It may also be the result of an inclination of the travel surface on which the device is to roll.

In order to obtain a comparative measurement of rolling resistances, the device in accordance with the invention will advantageously be provided with a handling arm serving as lever, which is firmly fastened to the hub or hubs or the disk or disks of the mounted assemblies by means capable of maintaining the center of gravity at the desired angular position.

When the device is at rest, this handling arm is preferably located in the plane which contains the center line of the axle connecting the centers of rotation of the assemblies and is perpendicular to the travel surface on which the device is to roll, and is firmly fastened to the axle connecting the two mounted assemblies, the axle being then rotationally integral with the hubs, and the ballasting means being firmly attached to the axle.

In case of the measurement of the adherence limit of a given tire, the device in accordance with the invention comprises an axle which connects the centers of rotation of the assemblies and is provided with at least one pulley for the winding of a traction cable, the pulley being fastened firmly to said axle, fixed in rotation on it. The application of a traction force on the cable by customary known means permits the placing in rotation of the device as well as the placing in movement of the center of gravity G of the device.

In accordance with the invention, a first process which permits the comparative measurement of rolling resistances of two sets of tires on the same travel surface consists in using two devices such as described above, a first device which is equipped with a first of set of tires which are identical to each other, and a second device equipped with a second set of tires which are identical to each other but different from the tires equipping the first device, placing the two devices on the same travel surface, assuring the load necessary for each of the devices by the ballasting means, imparting a cycloidal movement to the centers of gravity of the two devices by the placing in rotation of the two devices until obtaining the same angular position of the centers of gravity, blocking said centers in that position, and giving them freedom of movement at the same time.

Upon the identical rising of the centers of gravity of the two devices due to the rolling of said devices, the same potential energies have been stored. Upon the release of the devices, they are imparted a dampened rolling pendulum movement, the damping being due to the rolling resistance of the tires equipping the devices, this damping being proportional to the rolling resistance. As the devices of preferred use are provided with a handling arm which causes the placing in rotation, the blocking of the devices in a given position is advantageously assured by said arms, which are hooked or anchored to the travel surface.

The comparative measurement is preferably effected by comparison of the number of oscillations experienced respectively by each device which is equipped with a set of tires to be compared, the number of oscillations in a given period of time, or the number of oscillations until the stopping of the device.

In accordance with the invention, a second process which permits the comparative measurement of the adherence limits of sets of tires on the same travel surface consists in using at least two devices such as those described, a first device being equipped with a first set of tires which are identical to each other, the second device being equipped with a second set of tires which are identical to each other but different from the tires of the first set, placing the devices on the same travel surface, assuring the load necessary for each of the devices by the ballasting means, exerting a resultant traction force on each of the devices by means of at least one traction cable wound on a winding pulley which is rigidly fastened to the axle of rotation of the device until obtaining slippage between the set of tires and the travel surface.

The comparison of the adherence limits can be effected by viewing the handling bars of the two devices, which then serve as measurement needles, but it is preferably effected by reading the applied forces by means of dynamometers placed on the traction cable or cables.

If one calls the comparative measurements described measurements carried out in parallel, these same measurements can also be carried out in series by means of a single device, with which a first measurement is carried out with a first set of tires and then a second measurement with a second set of tires.

DESCRIPTION OF THE DRAWINGS

The characteristics and advantages of the invention will be better understood by means of the following description with refers to the drawing, showing embodiments of the invention byway of illustration and not of limitation. In the drawing.

DESCRIPTION OF PREFERRED EMBODIMENTS

Figure 1:
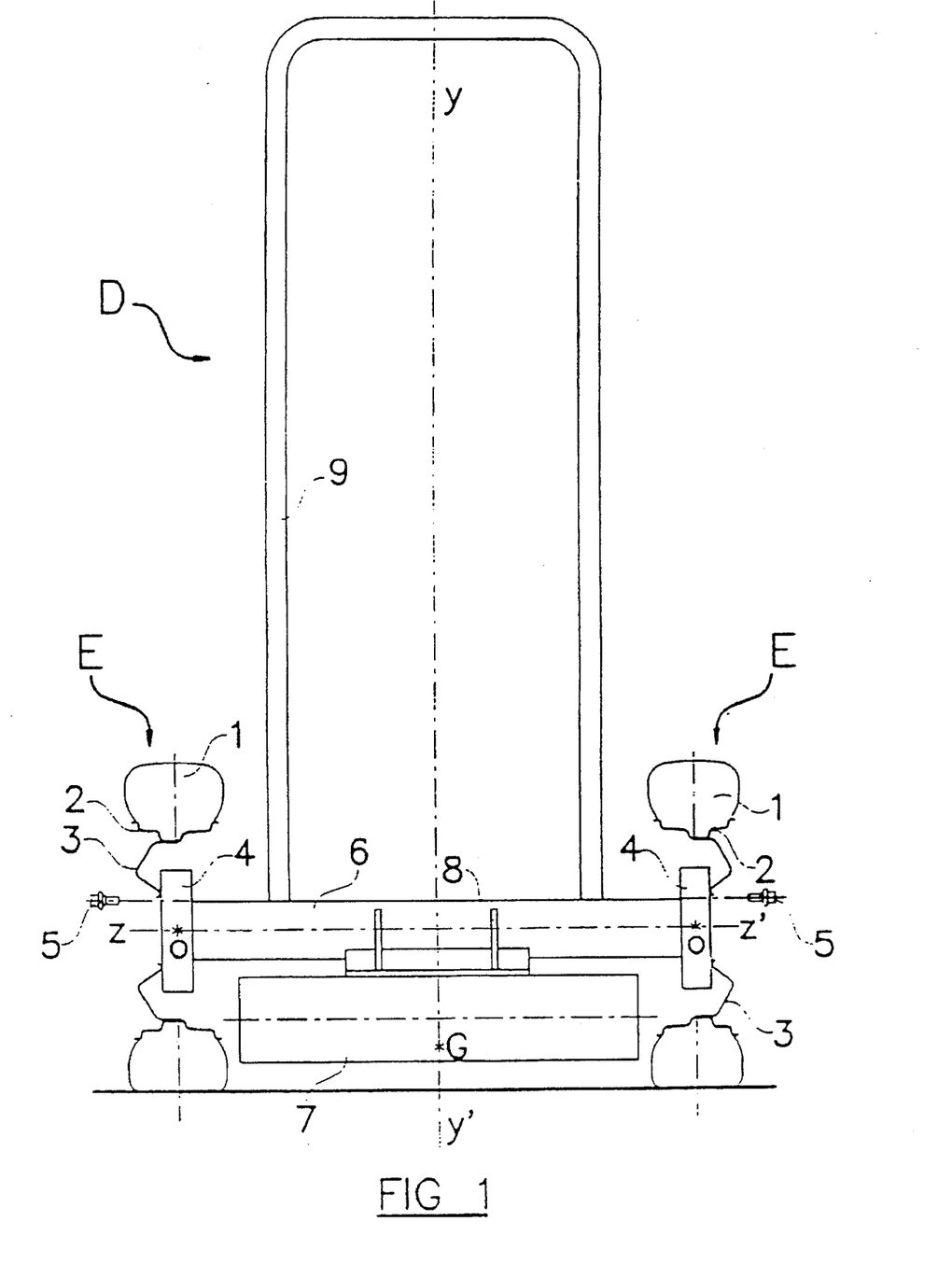
FIG. 1 diagrammatically shows a first variant of the device in accordance with the invention.

The device D, shown in FIG. 1 in accordance with the invention, comprises two mounted assemblies which are identical to each other. Each of these assemblies E is formed of a tire 1 mounted on its rim 2 and inflated to its test pressure. The rim 2 is attached to a hub 4 by a disk 3 which is assembled to the hub by means of the fastening screws 5. The two hubs are joined by an axle 6 of circular cross section which, in the example described, is rigidly fastened to the hubs 4, the axle 6 therefore being unable to turn freely with respect to the hubs 4. The axle 6 is provided with a load carrier 7, which is a nacelle or load carrier in which parts of cast iron or pig iron are fastened which are intended to assure symmetrically the desired load on the mounted assemblies E. This load carrier 7 is firmly fastened to the axle by means of brackets 8, so that, in the state of rest, the center of gravity G of the device is definitely radially below the axis ZZ' connecting the two centers of rotation O of the mounted assemblies E respectively. The axle 6 is furthermore provided with a handling arm 9 which is, in fact, a bar of inverted U shape, said bar being rigidly fastened to the axle 6 and being intended to place the device D in rotation.

Figure 2:
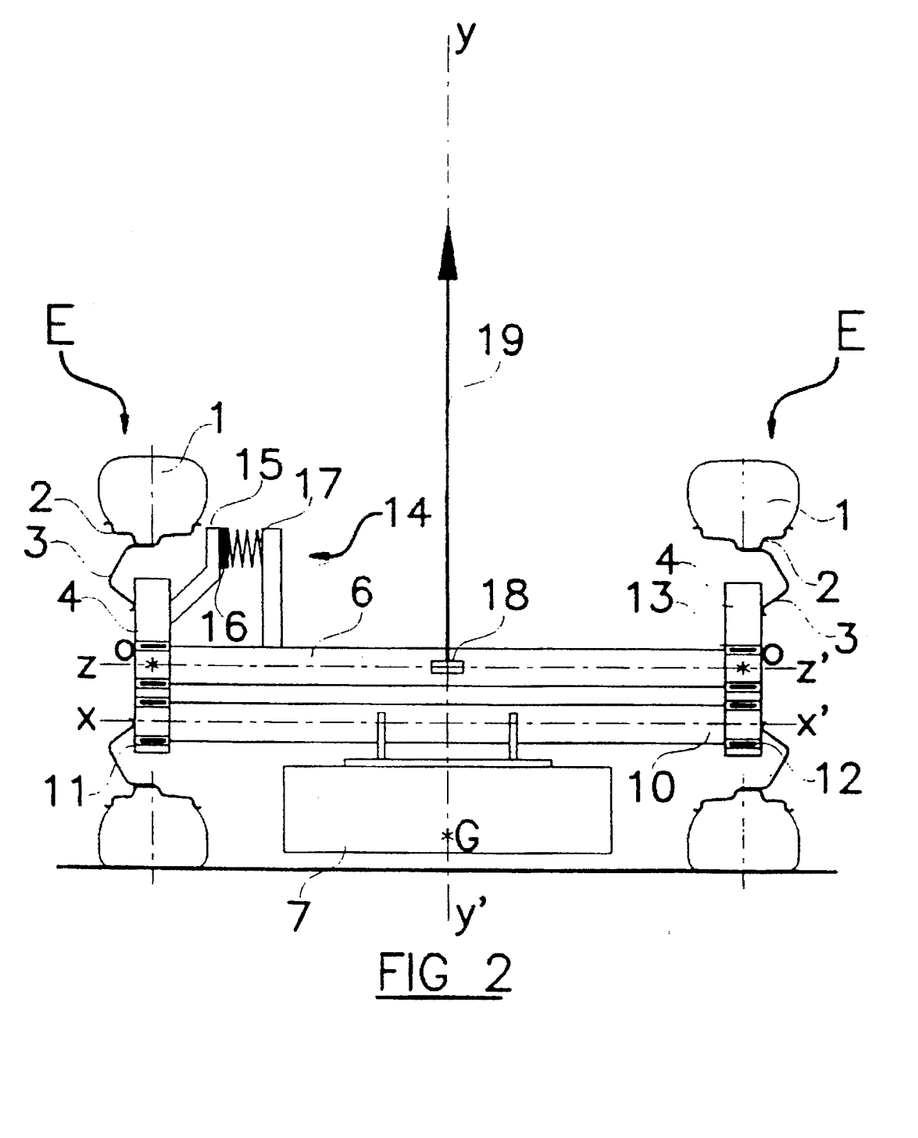
FIG. 2 shows, also diagrammatically, a second variant of said device.

One variant of the device in accordance with the invention is shown in FIG. 2. This device D differs from that shown in FIG. 1 primarily by the fact that the connecting arm 10 on which the load-holding load carrier 7 is firmly attached and which connects the two hubs 4, (the same reference numerals will be used in the case of identical parts in the two figures) does not have its axis of symmetry XX' identical with the axis of symmetry ZZ' of the axle 6 connecting the two centers of rotation 0 of the mounted assemblies E. This connecting arm or articulation arm can turn freely in housings 11 provided for this purpose in the hubs 4, in which housings the bearings 12 are disposed. The same is true of the axle 6 which, as could be the case in FIG. 1, can turn freely in the housings 13, but it can also be blocked by a device 14 formed of friction linings 15 onto which plates 16 can be applied under the effect of clamping forces caused by the compression of the springs 17. The movement in rotation of the device of FIG. 2 is assured by a traction force acting on a traction element 18 which may be a bar, a cord, or a metal cable, fastened firmly to the axle 6, but which can easily and instantaneously detach itself therefrom when it is desired to release the device. The traction force is exerted by any known mechanical device, such as a manual or mechanized winch or, more simply, by hand. On the axle 6, which will be blocked during the measurement of rolling resistance, there is fastened a measurement needle 19 which makes it possible to visualize the perpendicular movement of the center of gravity G of the device and to count the number of oscillations until the complete stopping of the pendulum movement.

Figure 3:
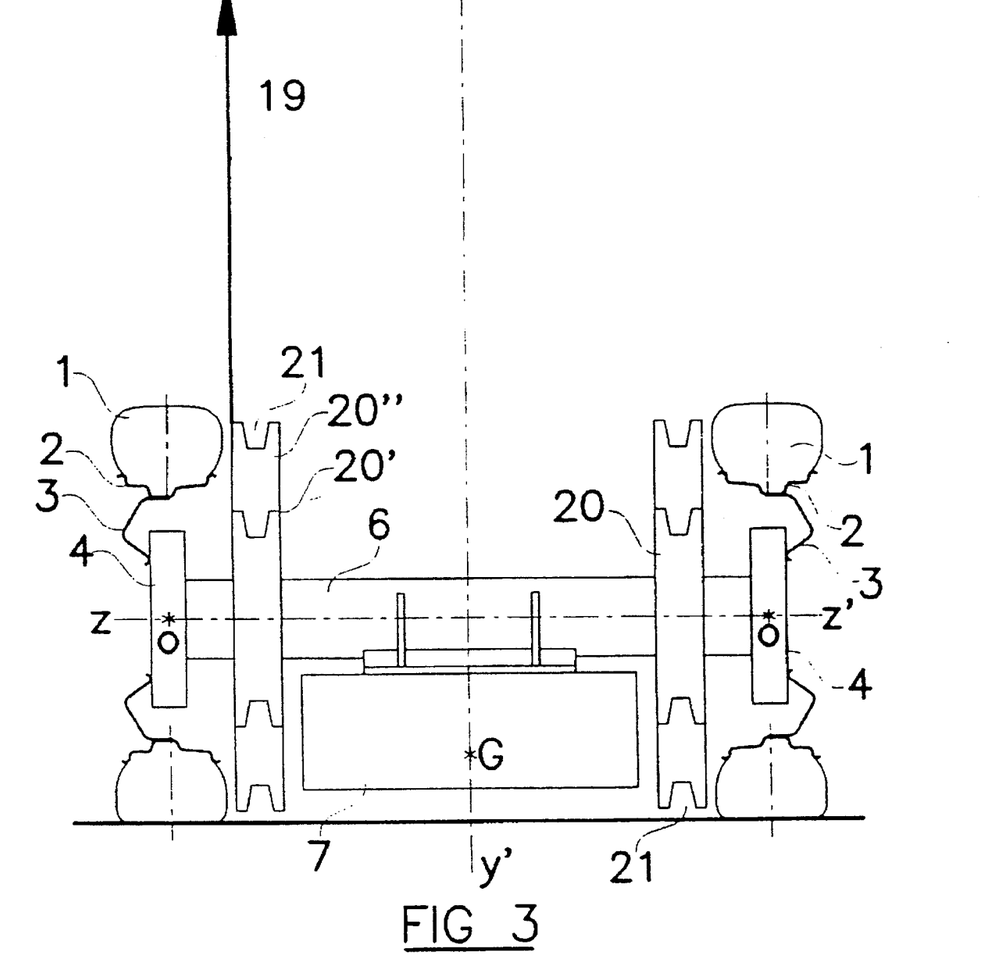
FIG. 3 diagrammatically shows a third variant of said device.

The variant of the device in accordance with the invention shown in FIG. 3 is substantially equivalent to that shown in FIG. 1. However, it differs from it by the following features: The connecting arm 10 which is identical with the axle 6 of rotation of the device D is provided with two pulleys 20, themselves provided with grooves 21 in which a traction cable is wound. These pulleys 20 are rigidly fastened to the axle 6 by any suitable manner of attachment, such as screws, bolts, etc.

The pulleys 20 can be of variable diameter, they being advantageously formed by the placing and fastening on a cylindrical part 20' of cylindrical rings 20" provided with grooves. One of the pulleys 20 is provided with a measurement needle 19, as described above.

Figure 4:
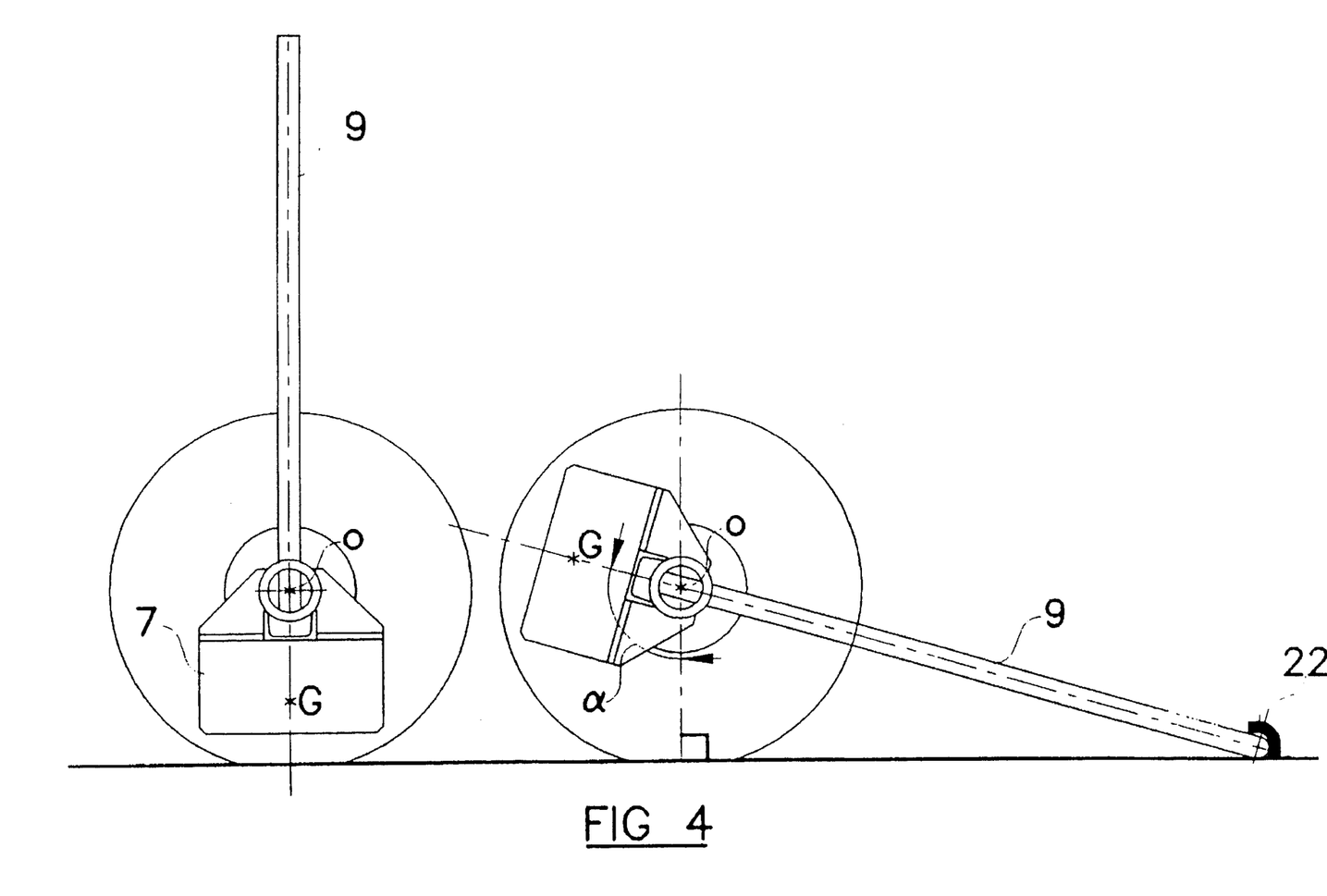
FIG. 4 diagrammatically shows the apparatus shown in FIG. 1, used in the process of measuring the rolling resistance.

In FIG. 4, the device of FIG. 1 is shown, on the one hand free at rest and, on the other hand, after the placing in starting position of the center of gravity G of the device. For the comparative measurement of the rolling resistances of two sets of tires which differ from each other either by characteristics of construction or by characteristics of use (pressure, load, etc.), two devices D, similar to the one shown in FIG. 1, are used and are placed one alongside of the other on the same travel surface. The two devices D are imparted a movement of rotation by manual application of a moment of rotation by means of the handling bar 9 with which each device is equipped, the movement of rotation being continued until the handling bar of each device is caught on a hook 22 which is anchored on the travel surface during this rotation, the centers of gravity G (which are at the same distance from the axes of rotation 00 if the loads are equal for the two devices) or G' and G" (which will be at a different distances from axes 00 if the loads for the two devices are different) describe more or less shortened cycloids, in such a manner that each center of gravity defines with the trace 0, on the plane of the figure, of the axes 00, a straight line forming an identical angle α for the two devices with the direction perpendicular to the travel surface and passing through the center 0 when the bars 9 are hooked by means of the hooks 22 fastened to the travel surface. At the same moment T, the two handling bars 9 are unhooked and the two devices are then imparted a pendulum movement which is dampened as a function of the total rolling resistances, including the rolling resistances of the tires.

In order to have a dependable comparison, it is recommended to carry out with rotation of sets of tires, a first measurement effected with the tires A on the device $D_1$ while the tires B are mounted on the device $D_2$ and a second measurement being effected immediately after the first with the tires A on the device $D_2$, and a second measurement being immediately carried out after the first with the tires A on the device $D_2$ and the tires B on the device $D_1$. The difference in rolling resistances which is measured between the two sets can be noted, for instance, by the number of oscillations effected by the bars 9 of the two devices respectively until the complete stopping of the pendulum movements, the total distances traversed by the ends of the arms 9 radially furthest from the centers of rotation 0 being inversely proportional to the rolling resistances of the tires A and B.

It is obvious that the process described for comparing two sets of tires is just as valid for comparing two or more types of travel surfaces, which differ in their characteristics, and, in particular, those characteristics which influence the rolling resistance. It is sufficient to take four reference tires which are identical to each other and which are preferably solid rubber tires of small height and have the two or more devices D roll simultaneously on the two or more different travel surfaces.

Figure 5:
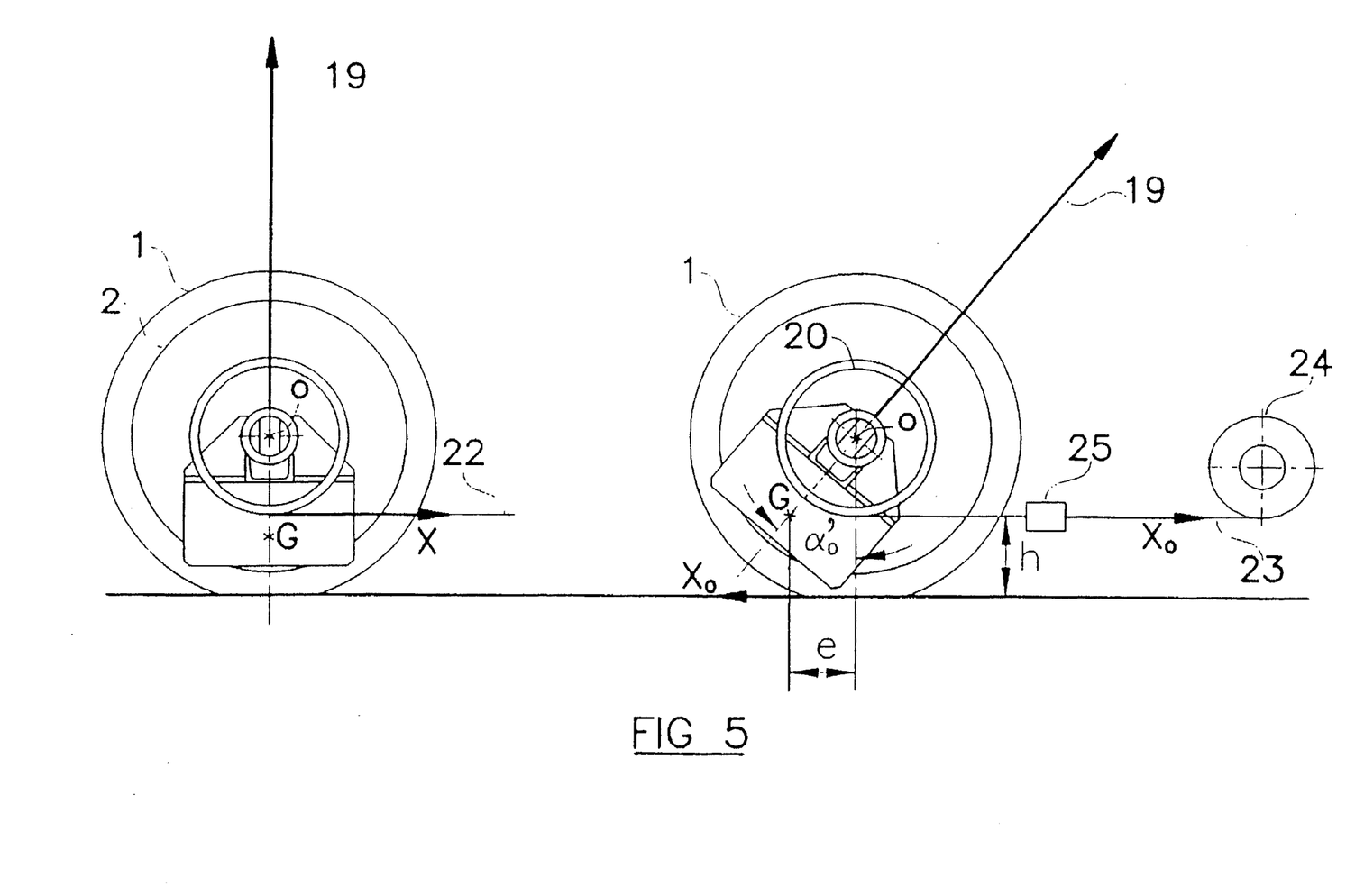
FIG. 5 diagrammatically shows the apparatus of FIG. 3 and its use in the process of measuring adherence limits.

In FIG. 5, the conditions for the use of the two or more devices necessary in order to compare the adherence limits of two or more sets of tires are explained. The devices used are preferably the devices shown in FIG. 3. The process of measurement differs, in principle, from the preceding one by the fact that a moment of rotation is applied to each device via a resultant traction force X applied on traction cables 23 wound in the grooves of two pulleys 20 of the device of FIG. 3, which pulleys are arranged symmetrically with respect to the plane of symmetry YY'. First of all, the application of this force X by means of a winch 24 at a distance h from the flat travel surface in the example described causes the movement of rotation of the device around the axis of rotation 00 in such a manner that the center of gravity G of the device, seen in section in the plane of symmetry YY' of the device, is located on a straight line GO which forms an angle α' perpendicular to the travel surface passing through 0, which angle is zero at the start of the movement and increases as a function of the applied force of traction X until reaching a value $α'_0$ for which the mounted assemblies will slip on the travel surface in question, the adherence limit being then reached for the set of tires in question, and the force of traction then being $X_0$. The angle $α'_0$ corresponds to a given axial distance e between the center of gravity G and the straight line bearing the reaction to the travel surface equal to the charge carried. It is possible to deduce therefrom the coefficient of adherence at the adherence limit as being equal to the ratio of the axial distance e to the radial distance h.

Figure 6:
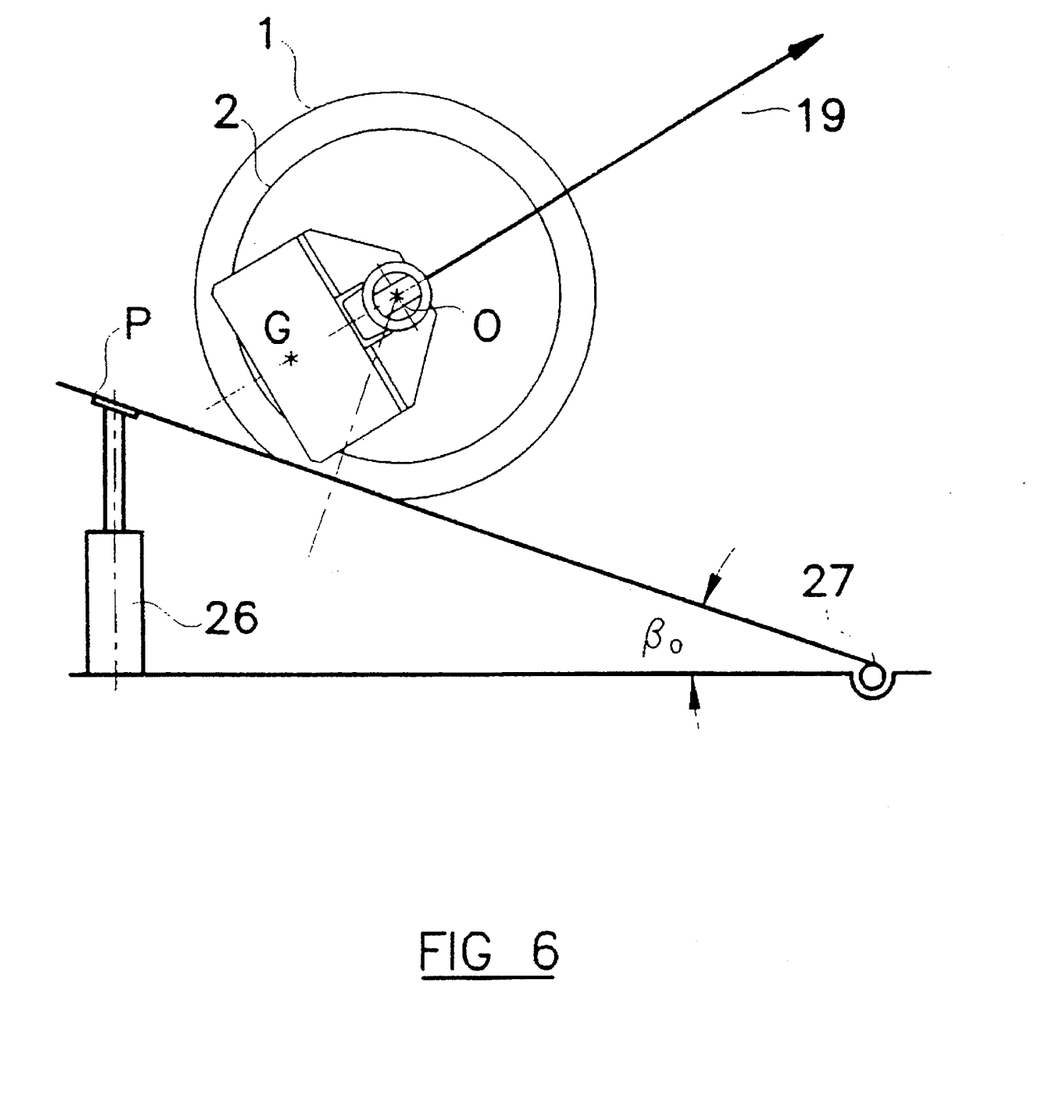
FIG. 6 diagrammatically shows the apparatus shown in FIG. 1 used in a different manner in the process of measuring adherence limits.

The comparative measurement can easily be visualized by the respective positions of the two measurement needles 19, but it can also advantageously be effected by means of dynamometers 25 placed on the traction cables 22, giving the values of the forces $X_0$ for the two sets of tires respectively, FIG. 6 also concerns a comparative measurement of the adherence limits, with the use of devices in accordance with the invention and more particularly of devices such as shown in FIGS. 1 and 2. The process differs from the process described previously in connection with FIG. 5 by the fact that the initial movement of rotation of the devices D and the sliding of the mounted assemblies E on the travel surface studied is caused not by a horizontal force of traction X exerted on one or more traction cables 22 by a suitable system but by the inclination β of inclined rolling planes P, said inclination being variable by the fact that the inclined planes P can be imparted a movement of rotation around axes 27 located at the level of the travel surface, for instance by means of jacks 26.

The devices D are initially placed on the rolling planes P in horizontal state. The planes P are then inclined at slow, constant speed, each device being then placed in rotation and then, for an angle $β_0$ of it rolling plane, the device slides on the plane. The comparative measurement of the two adherence limits can be effected by means of the measurement needles 19, but it is also possible to compare them by the respective angles $β_0$ of the two rolling planes P. A knowledge of these angles furthermore permits a calculation of the respective frictional forces of the two sets of tires.

Within the scope of the adherence limit measurements, it is also obvious that the comparisons can relate, not to sets of tires, but to travel surfaces which differ in their characteristics, whether flat travel surfaces or inclined travel surfaces, and in particular on travel surfaces differing in their lubrication.

It is also obvious that the dispersion of the measurements is minimized by rotation of sets of tires on the devices used as well as the rotation of devices on the travel surfaces to be compared.

I claim:

1. A device for measuring rolling resistances and/or adherence limits of sets of tires, characterized by the fact that it comprises at least two identical mounted assemblies E, assembled by a connecting arm having a center axis which is parallel to a straight line ZZ' joining centers of rotation O of the unloaded mounted assemblies, said connecting arm being provided with ballasting means (7) imposing a load on each of the assemblies E such that the center of gravity G of the device is located, at rest, between said straight line ZZ' and a travel surface on which the device will roll, the device also comprising means (9, 18, 20, P) capable upon rotation of the mounted assemblies E of imparting upon the center of gravity G a cycloidal movement enabling the center of gravity to assume a given angular position with respect to a plane containing the straight line ZZ' connecting the centers of rotation 0 of the mounted assemblies and perpendicular to the travel surface.

2. A device according to claim 1, characterized by the fact that the connecting arm is merged with an axle (6) defining the axis ZZ' connecting the centers of rotation 0 of the assemblies E.

3. A device according to claim 1, in which the assemblies include hubs (4) and an axle (6) defining the ZZ' is mounted to turn freely in the hubs (4) of the assemblies, and including means (14, 15, 16, 17) which permit the axle (6) to be fixed in rotation with the hubs (4).

4. A device according to claim 3, characterized by the fact that the means (18) which permit the application of a force of traction comprise a traction element (18) fastened on the center axis ZZ' of the axle (6) turning freely in the hubs (4), while being detachable from said axis, and the force of traction being assured manually or by a mechanical device.

5. A device according to claim 1, characterized by the fact that the means capable of imparting a cycloidal movement to its center of gravity G are means (18) which permit application of a traction force to the axle (6) of rotation of the device.

6. A device according to claim 1, characterized by the fact that the means capable of imparting a cycloidal movement to its center of gravity G are means (9, 20) which permit application of a moment of rotation to the two assemblies E.

7. A device according to claim 6, characterized by the fact that a hub (4) which permits application of a moment of rotation to the two assemblies is a handling bar (9) acting as lever arm, on which there is applied a force of manual or mechanical origin, and by the fact that the device comprises means (22) capable of maintaining said center of gravity G in desired angular position.

8. A device according to claim 6, characterized by the fact that the means (20) which permit application of the moment of rotation to the two assemblies are traction elements (22) wound in grooves (21) of pulleys (20), of a diameter other than zero such that the points of application of the traction forces applied are located in a plane containing the axis ZZ'.

9. A process of comparative measurement of the adherence limits of at least two sets of tires on the same travel surface, characterized by the fact that at least two devices according to claim 8 are used, a first device $D_1$ being equipped with a first pair of tires A which are identical to each other, a second device $D_2$ being equipped with a second pair of tires B which are identical to each other but different from the tires equipping the device $D_1$, the two loaded devices are placed on the same travel surface, a moment of rotation is applied to each device via a resultant traction force $X_0$ exerted on traction cables 22 wound in the grooves 21 of two pulleys 20 arranged symmetrically with respect to a plane of symmetry YY' of the device at a distance h from the travel surface and permitting sliding on the travel surface.

10. A device according to claim 1 characterized by the fact that the means capable of imparting a cycloidal movement to its center of gravity G is a rolling plane P inclined at an angle with respect to the travel surface, the angle of inclination β being variable as a function of time.

11. A process of comparative measurement of the adherence limits of at least two sets of tires on the same travel surface, characterized by the fact that at least two devices according to claim 10 are used, a first device $D_1$ being equipped with a first pair of tires A which are identical to each other, a second device $D_2$ being equipped with a second pair of tires B which are identical to each other but different from the tires equipping device $D_1$, each device is placed on a flat horizontal rolling surface P, each surface P is inclined until obtaining sliding of the device corresponding to said surface, the adherence limits being measured by the angles of inclination of the two inclined planes and comparison relating to the angles measured.

12. A process for the comparative measurement of the rolling resistances of at least two sets of tires on the same travel surface, characterized by the fact that at least two devices according to claim 1 are used, a first device $D_1$ being equipped with a first set of tires A which are identical to each other, a second device $D_2$ being equipped with a second set of tires B which are identical to each other but different from the tires A equipping the first device $D_1$, and by the fact that the two devices D, i.e. $D_1$ and $D_2$, are placed on the same travel surface with loads imposed by their respective ballasting means (7), a cycloidal movement is imparted to the centers of gravity G of the two devices D by the placing of the two devices in rotation until obtaining the same angular position α of the two centers of gravity G with respect to each plane perpendicular to the surface of the travel surface and containing an axis of rotation of each the two devices D respectively, said centers of gravity are retained in said position α and thereafter released at the same moment, dampings of pendulum movements of the two devices respectively being compared visually or by measurements.

13. A process of comparative measurement of the properties of at least two rolling surfaces, characterized by the use of at least two devices D according to claim 1, said devices being all equipped with solid rubber tires of slight height on the rim and which are identical to each other, by the fact that each device is placed on one of the rolling surfaces to be compared, the centers of gravity G of said devices which have been previously loaded are imparted a cycloidal movement by the placing in rotation of the two devices D until obtaining the same angular position α of the two centers of gravity G with respect to each plane perpendicular to the surface of the travel surface and containing an axis of rotation of each of the two devices D respectively, said centers of gravity are retained in said position α and thereafter are released at the same moment, the dampings of the pendulum movements of the two devices respectively being compared visually or by measurements.

* * * * *

UNITED STATES PATENT AND TRADEMARK OFFICE
CERTIFICATE OF CORRECTION

PATENT NO. : 5,635,623
DATED : June 3, 1997
INVENTOR(S) : Simon

It is certified that error appears in the above-indentified patent and that said Letters Patent is hereby corrected as shown below:

Col. 1, line 47, "a comparative measurements" should read --a comparative measurement--.
Col. 2, line 26, "manually of" should read --manually or--.
Col. 3, line 46, "with" should read --which--.
Col. 5, line 13, "at a" should read --at--.
Col. 6, line 37, "it" should read --its--.
Col. 7, line 10, "ZZ' " should read --axis ZZ' --;
line 35, "in desired" should read --in a desired--.
Col. 8, line 4, "angle with" should read --angle β with--;
line 34, "each the" should read --each of the--.

Signed and Sealed this

Eleventh Day of November, 1997

Attest:

Attesting Officer

BRUCE LEHMAN

Commissioner of Patents and Trademarks